US009974480B2

(12) United States Patent
Ike

(10) Patent No.: US 9,974,480 B2
(45) Date of Patent: May 22, 2018

(54) ARTERY VISUALIZATION DEVICE

(71) Applicant: PLUSMED CORPORATION, Kochi-shi, Kochi (JP)

(72) Inventor: Tatsumi Ike, Tosa (JP)

(73) Assignee: PLUSMED CORPORATION, Koichi (JP)

( * ) Notice: Subject to any disclaimer, the term of this patent is extended or adjusted under 35 U.S.C. 154(b) by 0 days. days.

(21) Appl. No.: 15/313,993

(22) PCT Filed: May 13, 2016

(86) PCT No.: PCT/JP2016/064352
§ 371 (c)(1),
(2) Date: Nov. 25, 2016

(87) PCT Pub. No.: WO2016/182075
PCT Pub. Date: Nov. 17, 2016

(65) Prior Publication Data
US 2017/0188937 A1 Jul. 6, 2017

(30) Foreign Application Priority Data

May 13, 2015 (JP) ................................. 2015-098174

(51) Int. Cl.
*A61B 5/00* (2006.01)
(52) U.S. Cl.
CPC ............ *A61B 5/489* (2013.01); *A61B 5/0059* (2013.01); *A61B 5/702* (2013.01)
(58) Field of Classification Search
CPC ......... A61B 5/00; A61B 5/702; A61B 5/6824; A61B 5/0086; A61B 5/0084; A61B 5/0059
See application file for complete search history.

(56) References Cited

U.S. PATENT DOCUMENTS

2002/0026121 A1* 2/2002 Kan ................... A61B 5/02116
600/500
2009/0054751 A1* 2/2009 Babashan ............ A61B 5/0002
600/324
(Continued)

FOREIGN PATENT DOCUMENTS

JP   2012-130584 A   7/2012
JP    5626943 B2    11/2014

OTHER PUBLICATIONS

Aug. 2, 2016 Written Opinion issued in International Patent Application No. PCT/JP2016/064352.
(Continued)

*Primary Examiner* — Tse Chen
*Assistant Examiner* — Jason Ip
(74) *Attorney, Agent, or Firm* — Oliff PLC

(57) ABSTRACT

An artery visualization device for irradiating skin on the wrist back side with near-infrared light and forming near-infrared image of the wrist includes a placement table on which the wrist is placed, an irradiation unit including a light source emitting near-infrared light, imaging unit receiving light and forming wrist near-infrared image, the light incidents on the skin on the wrist back side and exiting from skin on the front, optical filter, and monitor. The artery visualization device includes a protrusion protruding from a placement table wrist placement surface. The protrusion compresses the back side skin on the wrist placed on the placement table from the back side, and irradiates the near-infrared light emitted from the light source to the skin on the back. The placement table includes a center placement portion and back of hand contact portion. The back of hand contact surface intersects obliquely with a wrist placement surface.

9 Claims, 9 Drawing Sheets

(56) References Cited

U.S. PATENT DOCUMENTS

2012/0257034 A1* 10/2012 Shimokita ............ A61B 5/0059
    348/77
2015/0133791 A1    5/2015 Sato et al.

OTHER PUBLICATIONS

Aug. 2, 2016 International Search Report issued in International Patent Application No. PCT/JP2016/064352.
Oct. 25, 2016 Decision to Grant issued in Japanese Patent Application No. 2016-556345.

* cited by examiner

A-A Cross-sectional View

B-B Cross-sectional View

B-B Cross-sectional View

ARTERY VISUALIZATION DEVICE

TECHNICAL FIELD

The present invention relates to a visualization device of the arteries in the wrist.

BACKGROUND ART

In a test or treatment using a catheter, such as a cardiac catheter test, an artery is punctured, and a guide wire and a catheter are inserted. Examples of the puncture site include the radial artery, the brachial artery, and the femoral artery. Among such arteries, the radial artery is easy to provide hemostasis and rest after the test and does not need a restriction on the patient's activities, and is thus suitable as the puncture site.

A high level of skill is needed to puncture the radial artery. A puncture of the radial artery is typically performed by estimating the running of the radial artery by palpation. If difficult, a puncture may be performed by using an ultrasonic diagnostic device. To perform a procedure while scanning a probe is troublesome. In addition, an ultrasonic diagnostic device is relatively expensive. From such a clinical background, a simple and relatively inexpensive technique for visualizing various arteries, particularly the radial artery, has been desired.

As a technical approach, there has been proposed an artery visualization device that uses the property that human tissues such as skin, fat, and muscle are highly transmissive to near-infrared light, but hemoglobin in blood absorbs near-infrared rays (Patent Literature 1). In this artery visualization device, the skin on the back side of the wrist is irradiated with near-infrared light from a light guide portion, and the near-infrared light transmitted through the wrist is received on the front side of the wrist to form a near-infrared image of the arteries of the wrist. To prevent the near-infrared light from being absorbed by the capillary plexus to make the image of the arteries unclear, the skin on the back side of the wrist is compressed by the light guide portion at appropriate pressure to collapse the capillary plexus in the skin on the back side of the wrist. The artery visualization device thus includes a pressure sensor for performing the compression by the light guide portion at appropriate pressure, and, if necessary, a pressure adjustment unit such as a balloon.

CITATION LIST

Patent Literature

Patent Literature 1: Japanese Patent No. 5626943

SUMMARY OF INVENTION

Technical Problem

However, it is troublesome to measure the pressure at which the light guide portion compresses the skin with the pressure sensor, adjust the pressure at which the light guide portion compresses the skin with the pressure adjustment unit, and at the same time observe the near-infrared image of the wrist while performing artery puncture.

It is thus an object of the present invention to provide a new technique for compressing the skin on the back side of the wrist at appropriate pressure by a simple configuration when irradiating the skin with near-infrared light and receiving the near-infrared light transmitted through the wrist on the front side of the wrist to form a near-infrared image of the wrist.

Solution to Problem

The present inventor has found the following and conceived the present invention: if a placement table on which the wrist is placed is formed in a specific shape, a protrusion for compressing the skin on the back side of the wrist is protruded from a placement surface of the placement table, and near-infrared light is made incident on the skin on the back side of the wrist from the protrusion, then the skin on the back side of the wrist can be appropriately compressed by the protrusion and the capillary plexus in the skin of that part can be collapsed to obtain a clear image of the arteries by simply placing the hand with the back of the hand along the placement surface of the placement table.

More specifically, the present invention provides an artery imaging device including:

a placement table on which a wrist is place;

an irradiation unit including a light source that emits near-infrared light;

an imaging unit for receiving light and forming a near-infrared image of the wrist, the light being incident on skin on a back side of the wrist and exiting from skin on a front side; and an optical filter that is arranged in front of a light receiving surface of an image sensor of the imaging unit, the optical filter being for transmitting near-infrared light, and cutting off visible light, wherein the placement table includes a center placement portion and a back of hand contact portion with which the back of the hand makes contact, the artery imaging device includes a protrusion protruding from a wrist placement surface of the placement table, the protrusion compressing the skin on the back side of the wrist placed on the placement table from the back side of the wrist and irradiating the near-infrared light emitted from the light source to the skin on the back side, and in a vertical cross section passing through the protrusion and longitudinally sectioning the placement table, a back of hand contact surface of the back of hand contact portion intersects obliquely with a wrist placement surface of the center placement portion, and, with respect to an end of the back of hand contact portion on a side of the center placement portion, an end of the back of hand contact portion on an opposite side lies below.

The present invention also provides an artery visualization device including the foregoing artery imaging device and a monitor for displaying a near-infrared image of an artery, formed by the artery imaging device.

Advantageous Effects of Invention

In the artery imaging device according to the present invention, the placement table of the wrist is provided so that the protrusion for irradiating near-infrared rays protrudes from the placement surface of the wrist. The wrist can thus be stably placed on the protrusion.

The placement table includes the center placement portion from which the protrusion protrudes, and the back of hand contact portion with which the back of the hand makes contact. The wrist placement surface of the center placement portion and the back of hand contact surface of the back of hand contact portion intersect obliquely so that the fingertip side lowers if the wrist is placed on the center placement portion. Unlike when the vicinity of the wrist is placed on a flat plate with the back of the hand downward, the wrist therefore will not lift up from the placement table.

Moreover, if the wrist is placed on the center placement portion and the back of the hand is brought into contact with the back of hand contact portion, the back side of the wrist naturally presses the center placement portion. The skin on the back side of the wrist is thus appropriately compressed by the protrusion, and the capillary plexus in that part is collapsed. Consequently, a clear artery image capable of observation of artery pulsation can be obtained to perform safe puncture without using a pressure sensor.

According to the artery visualization device of the present invention, the near-infrared image of the arteries of the wrist, formed by the artery imaging device of the present invention, can be observed on the monitor.

DESCRIPTION OF EMBODIMENTS

Figure 1:
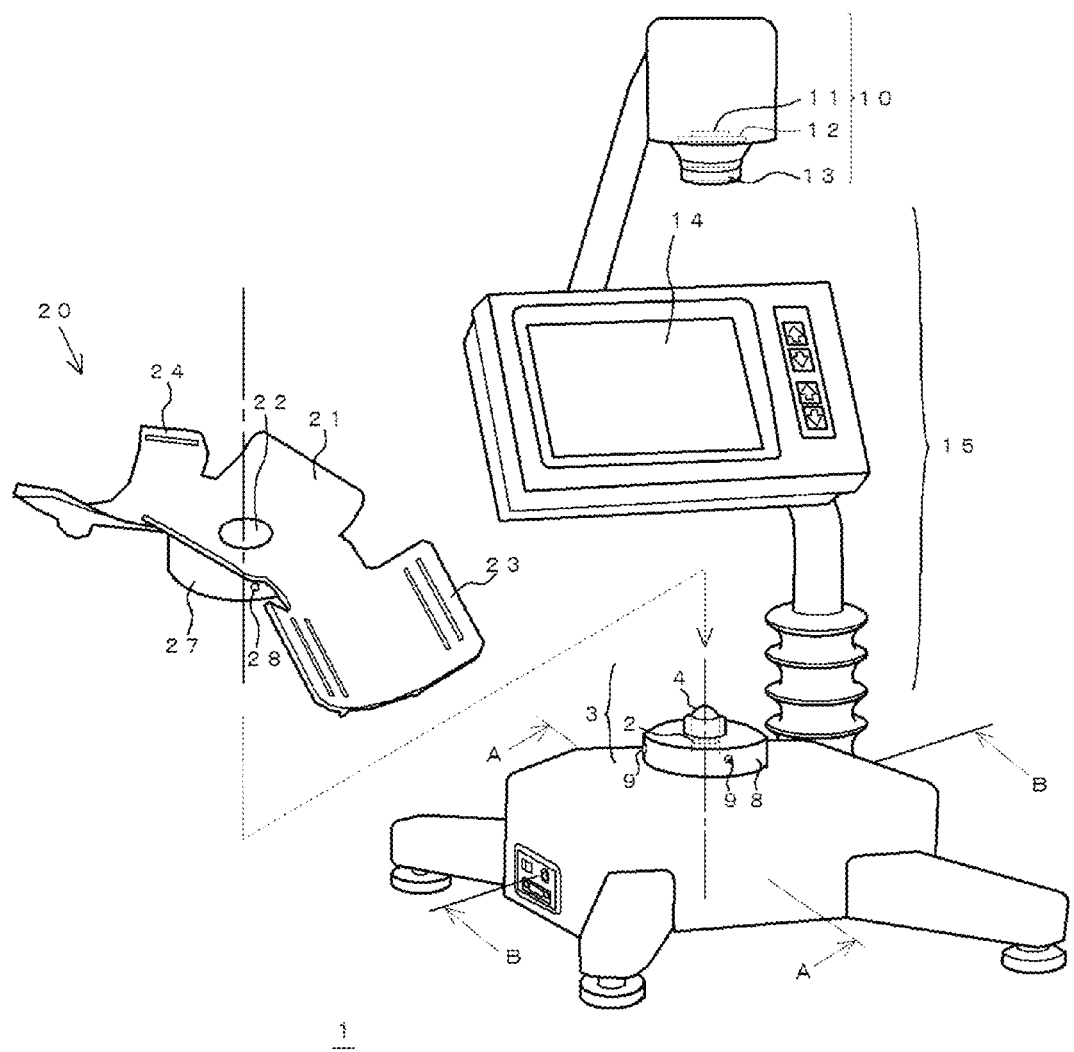
FIG. 1 is a perspective view of an artery visualization device according to an embodiment.

The present invention will be described in detail below with reference to the drawings. In the drawings, the same reference numerals represent the same or similar components.

Figure 2:
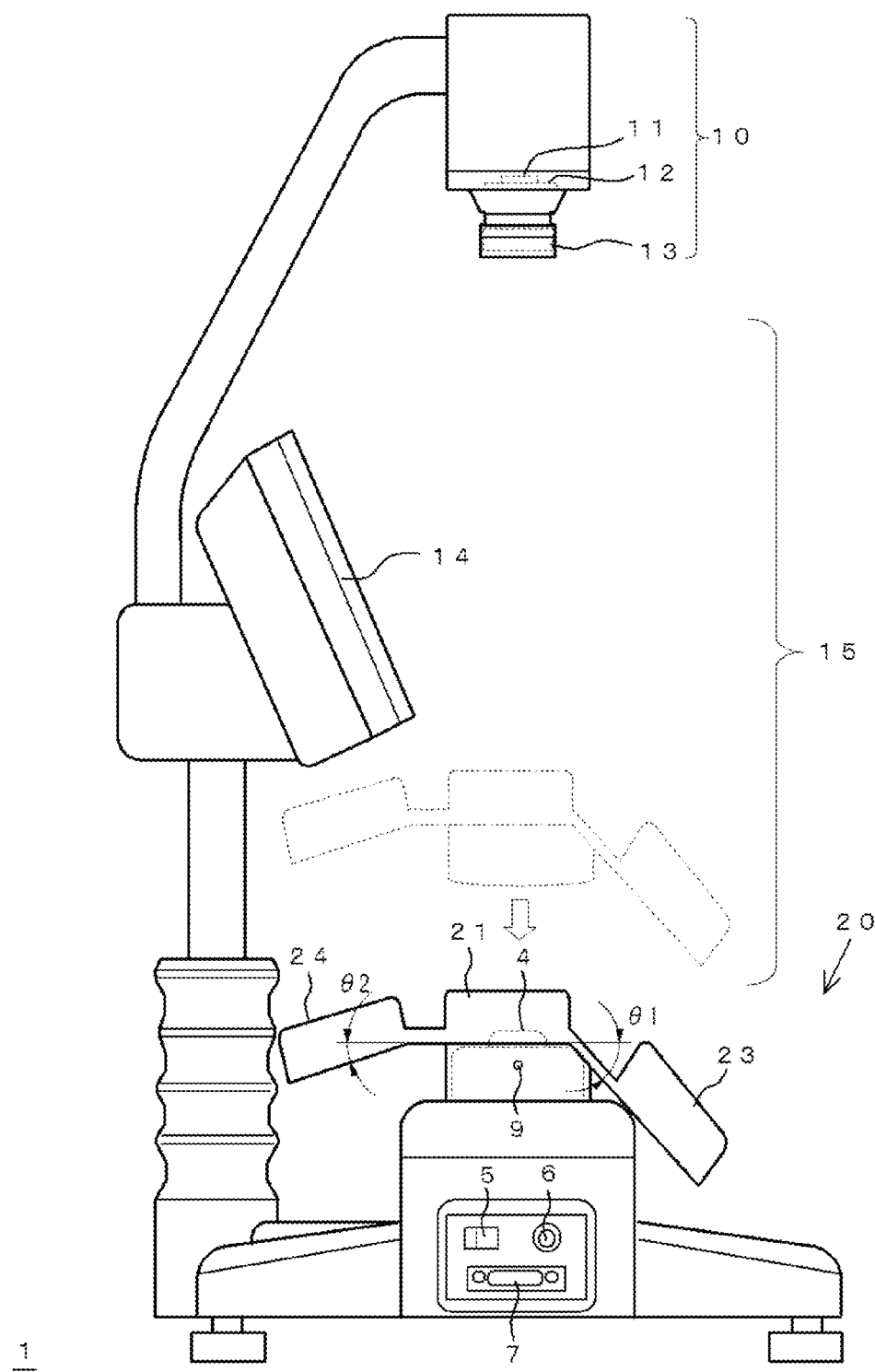
FIG. 2 is a side view of the artery visualization device according to the embodiment.

FIG. 1 is a perspective view of an artery visualization device 1 according to an embodiment of the present invention. FIG. 2 is a side view of the same.

This artery visualization device 1 generally includes a placement table 20 on which a wrist is placed, an irradiation unit 3 including a light source 2 for emitting near-infrared light, an artery imaging device including an imaging unit 10 which forms a near-infrared image of the wrist, and a monitor 14.

In the present embodiment, the irradiation unit 3 includes a protrusion 4 which protrudes from a placement surface of the wrist of the placement table 20. This protrusion 4 compresses the skin on the back side of the wrist which is placed on the placement table 20 from the back side of the wrist (the back side of the hand), and irradiates the near-infrared light emitted from the light source 2 to the skin on the back side.

The imaging unit 10 receives the light that is incident on the skin on the back side of the wrist and exiting from the skin on the front side (palm side) of the wrist, and forms a near-infrared image of the wrist. More specifically, the imaging unit 10 includes an image sensor 11, an optical filter 12 which is arranged in front (on the light source side) of a light receiving surface thereof, transmits near-infrared light, and cuts off visible light, and a single-focus lens 13 capable of near-infrared rays. A working space 15 in which puncturing can be performed on the arteries of the wrist placed on the placement table 20 is provided between the placement table 20 and the imaging unit 10.

As employed herein, the light source 2 of the irradiation unit 3, the imaging unit 10, and the monitor 14 may be configured in a manner similar to the artery visualization device described in Japanese Patent No. 5626943 (Patent Literature 1).

For example, an LED or the like that emits near-infrared light of 840 nm to 950 nm in wavelength may be used as the light source 2.

In the present embodiment, if the light source 2 emits diffused light, the protrusion 4 arranged on the irradiation unit 3 may be made of a glass or resin convex lens that transmits near-infrared light. The near-infrared light emitted from the light source 2 using an LED can thus be formed into parallel light and made incident on the wrist placed on the placement table 20, whereby the near-infrared image can be made clear.

If the protrusion 4 of the irradiation unit 3 is made of a convex lens, a filling agent may be filled in between the convex lens and the light source 2 if needed.

The imaging unit 10 may include a CCD camera or CMOS camera using a near-infrared CCD or CMOS as the image sensor 11. Data captured by the imaging unit 10 is subjected to image processing and image analysis such as noise processing, edge processing, and contrast enhancement, and thereby converted into image data to be displayed on the monitor 14.

A power switch 5, a DC jack 6, and an output terminal 7 of a video signal are provided on a main body housing of the artery visualization device 1. A video signal can be taken out from the output terminal 7 to observe an image on an external monitor or transmit an image signal over a communication line.

A characteristic configuration of this artery visualization device 1 is that the placement table 20 has a specific shape and the placement table 20 is formed to allow the protrusion 4 to protrude. More specifically, a center placement portion 21 of the placement table 20 has an opening 22 in the center. If the placement table 20 is attached to the irradiation unit 3, the center placement portion 21 allows the protrusion 4 of the irradiation unit 3 to protrude. The placement table 20 also includes a back of hand contact portion 23 with which the back of the hand makes contact if the wrist is placed on the center placement portion 21 of the placement table 20 with the back side of the wrist downward.

Figure 4A:
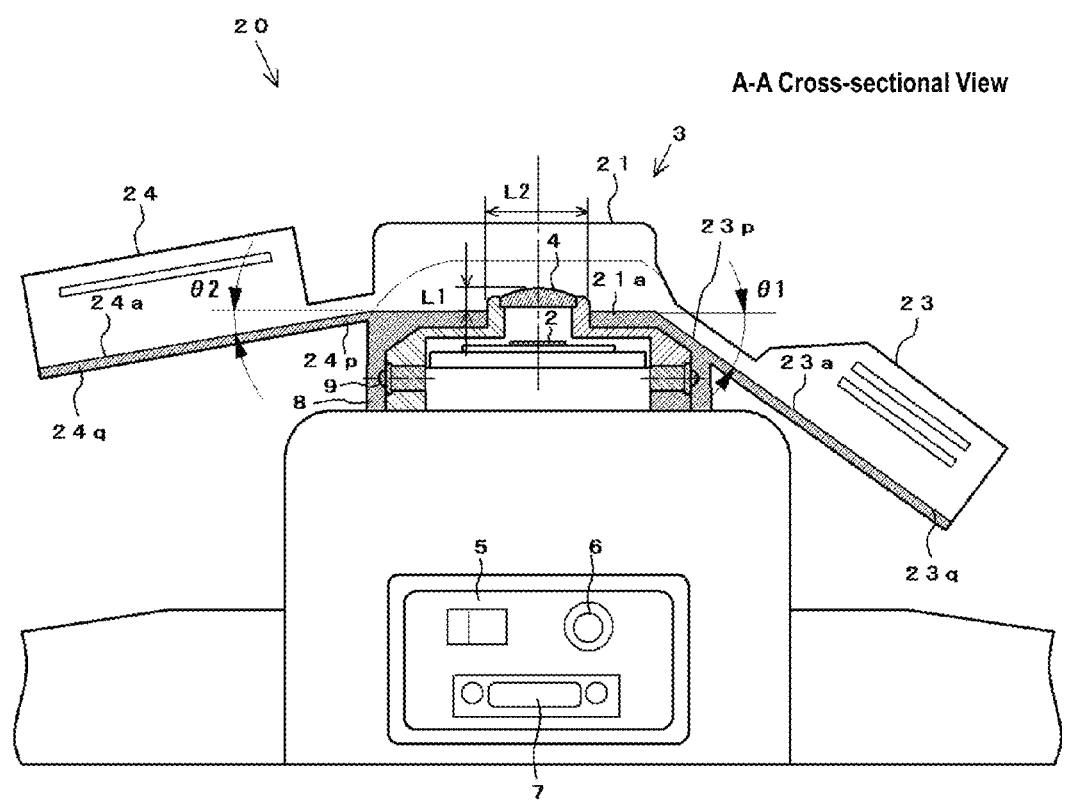
FIG. 4A is an A-A cross-sectional view of the wrist plate attached to a protrusion of an irradiation unit.

As shown in FIG. 4A, in a vertical cross section of the placement table 20 passing through the center of the protrusion 4 of the irradiation unit 3 and longitudinally sectioning the placement table 20, a back of hand contact surface 23a of the back of hand contact portion 23 intersects obliquely with a wrist placement surface 21a of the center placement portion 21. With respect to an end 23p of the back of hand contact portion 23 on the center placement portion side, an end 23q of the back of hand contact portion on the opposite side lies below.

In general, if the region from the forearm to the hand is placed on a flat plate with the back of the hand downward and the wrist is fixed in an extended position, the forearm more proximal than the wrist joint tends to lift up. In such a state, even if the back side of the wrist is irradiated with the near-infrared light from the protrusion 4 of the irradiation unit 3, the skin on the back side is not able to be effectively compressed by the protrusion 4 of the irradiation unit 3 and the capillary plexus in this part is not able to be collapsed. In contrast, as shown in FIG. 4A, with the back of hand contact portion 23 tilted from the center placement portion 21, the test subject places the wrist on the center placement portion 21 and attempts to bring the back of the hand into contact with the back of hand contact portion 23. The wrist therefore does not lift up from the placement surface 21a of the center placement portion 21, and the back of the wrist is pressed against the protrusion 4 of the irradiation unit 3 protruding from the center placement portion 21 by its own weight. This naturally provides an appropriate contact pressure of 20 mmHg to 40 mmHg without measuring the contact pressure of the protrusion 4 of the irradiation unit 3 by a pressure sensor. Consequently, the capillary plexus in the skin on the back side of the wrist is collapsed and a clear near-infrared absorption image of the arteries can be obtained, so that pulses in the radial artery and the ulnar artery can be observed.

Here, an angle θ1 formed between the back of hand contact surface 23a of the back of hand contact portion 23 and the wrist placement surface 21a of the center placement portion 21 is preferably 30° to 75°, and more preferably 30° to 40°. If the angle θ1 is too small or too large, or close to 90° in particular, the subject who places the wrist on the center placement portion 21 tends to not bring the back of the hand into contact with the back of hand contact portion 23. This makes it difficult for the protrusion 4 to reliably compress the skin on the back side of the wrist.

Figure 4B:
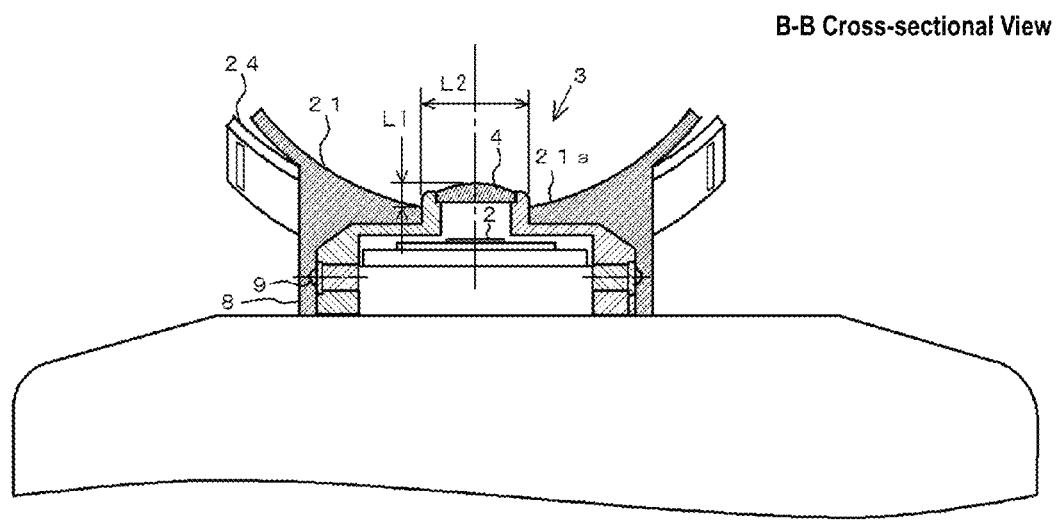
FIG. 4B is a B-B cross-sectional view of the wrist plate attached to the protrusion of the irradiation unit.

To stably place the wrist on the protrusion 4 of the irradiation unit 3, as shown in FIG. 4B, the wrist placement surface 21a of the center placement portion 21 is preferably curved into a gutter shape having a U-shaped cross section.

To clarify the near-infrared image of the arteries, in the vicinity of the protrusion 4 protruding from the center placement portion 21, the protrusion 4 preferably has a protruding height L1 of 5 mm to 10 mm from the wrist placement surface 21a. The protrusion 4 preferably has a diameter L2 of 5 mm to 15 mm. The position of the protrusion 4 in the center placement portion 21 may be at the center of the center placement portion 21 in a width direction. The protrusion 4 may be formed in an extended shape in the width direction of the center placement portion 21 so that the protrusion 4 lies directly below the radial artery regardless of which wrist, the right or the left, is placed on the center placement portion 21.

To further clarify the near-infrared image of the arteries, the placement table 20 preferably includes a forearm placement portion 24 on which the region between the wrist and the elbow is placed. In the foregoing cross section shown in FIG. 4A, a forearm placement surface 24a of the forearm placement portion 24 is preferably arranged to intersect obliquely with the wrist placement surface 21a of the center placement portion 21. With respect to a center placement portion-side end 24p of the forearm placement portion 24, an end 24q of the forearm placement portion on the opposite side is preferably located below. If the wrist is placed on the center placement portion 21, the back of the hand is preferably put along the back of hand contact surface 23a and the forearm along the forearm placement surface 24a because the back side of the wrist is compressed by the protrusion 4 more strongly.

Here, an angle θ2 formed between the forearm placement surface 24a of the forearm placement portion 24 and the wrist placement surface 21a of the center placement portion 21 is preferably 5° to 30°.

The wrist placement surface 21a of the center placement portion 21 is preferably horizontal in view of facilitating a puncture by a practitioner who faces the subject.

The back of hand contact portion 23 and the forearm placement portion 24 are both preferably formed in a gutter shape having a U-shaped cross section so that the back of the hand and the forearm are placed in stable positions.

Figure 3A:
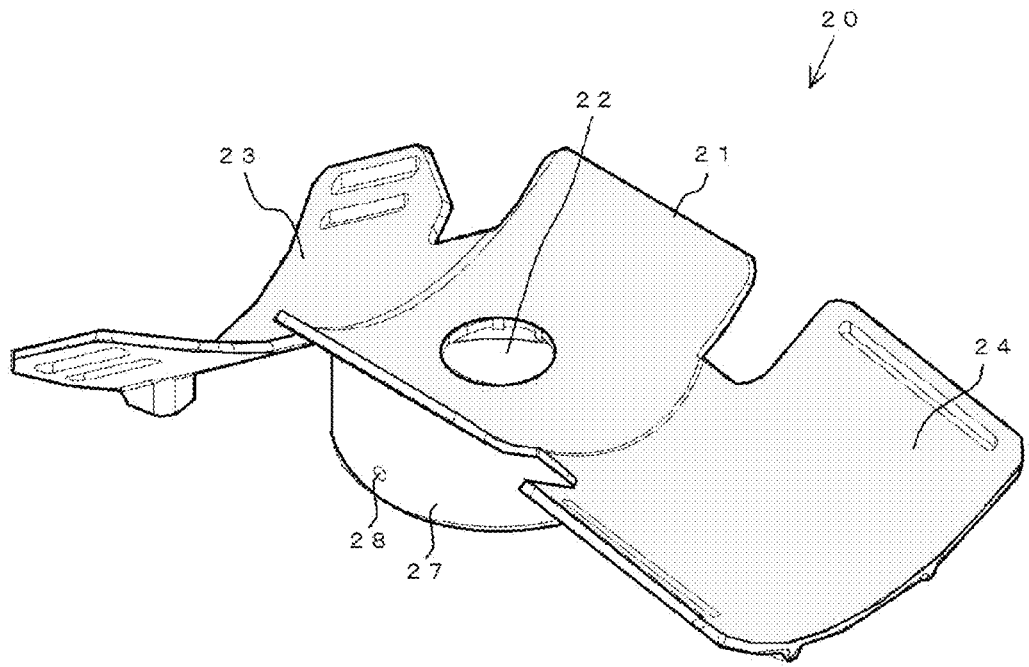
FIG. 3A is a perspective view of a wrist plate of the artery visualization device according to the embodiment.

For ease of handling, the center placement portion 21, the back of hand contact portion 23, and the forearm placement portion 24 constituting the placement table 20 are preferably formed as an integrally-molded wrist plate as shown in FIG. 3A, so that the portions are detachably attached to the protrusion 4 of the irradiation unit 3 as shown in FIGS. 1 and 2.

This facilitates the cleaning and disinfection of the placement table 20, and the placement table 20 can be kept clean.

Figure 3B:
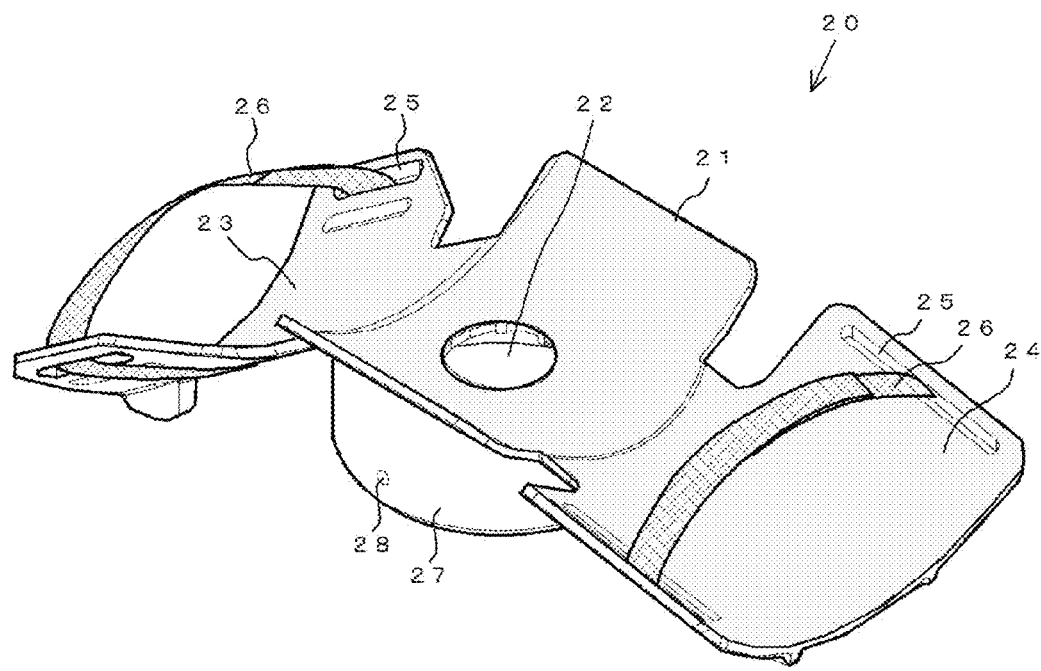
FIG. 3B is a perspective view of the wrist plate of the artery visualization device according to the embodiment.

The wrist plate 20 is preferably configured to be detachably attachable to the irradiation unit 3 and equipped with a belt for fixing the wrist. For example, as shown in FIG. 3B, a belt 26 using a hook-and-loop fastener is attached to slits 25 which extend in the longitudinal direction of the placement table 20. If the wrist is fixed to the wrist plate by this belt 26, an indwelling needle is put into an artery of the wrist, and then the wrist plate 20 is detached from the irradiation unit 3 with the wrist still fixed, the wrist plate 20 can be used as a splint.

To enable the use of the wrist plate as a splint by a plurality of subjects, a plurality of wrist plates are preferably provided for one artery imaging device.

As a method for detachably fixing the wrist plate 20 to the irradiation unit 3, for example, a lock mechanism may be provided between a seat 8 of the irradiation unit 3 and a seat 27 of the wrist plate 20 which is put over the seat 8. Specifically, press-fit plungers 9 are arranged on the side surface of the seat 8 of the irradiation unit 3. Holes 28 for the press-fit plungers 9 to fit in are formed in the seat 27 of the wrist plate 20.

The present invention may have various modes.

Figure 5:
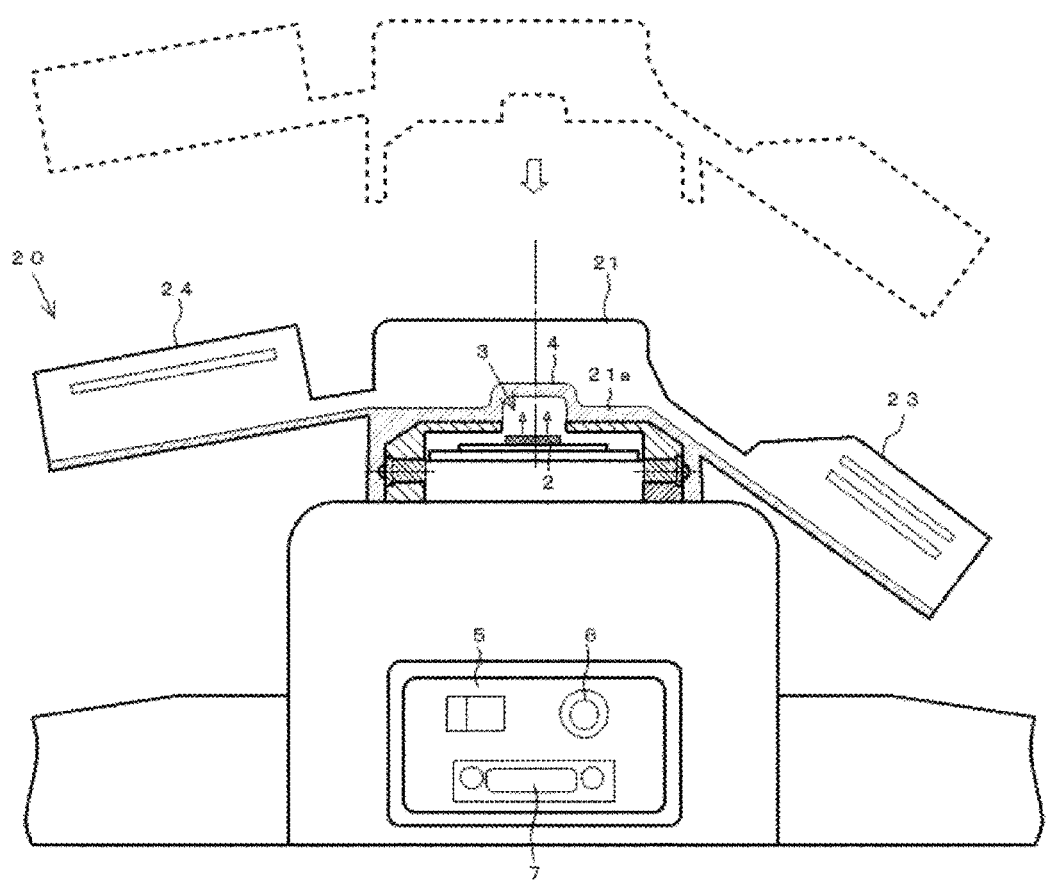
FIG. 5 is a cross-sectional view of a modified mode of the wrist plate.

For example, the placement table 20 may be fixedly installed over the light source 2. As shown in FIG. 5, the wrist placement surface 21a of the center placement portion 21 may be protruded to build the protrusion 4 in the center placement portion 21. The center placement portion 21 having such a protrusion 4, the back of hand contact portion 23, and the forearm placement portion 24 may be integrally molded into a wrist plate, and the wrist plate may be detachably attached to above the light source 2 of the irradiation unit 3.

An LED light source for emitting parallel light may be used as the light source 2 constituting the irradiation unit 3, and the protrusion 4 may be formed in the shape of a flat-topped column.

Figure 6A:
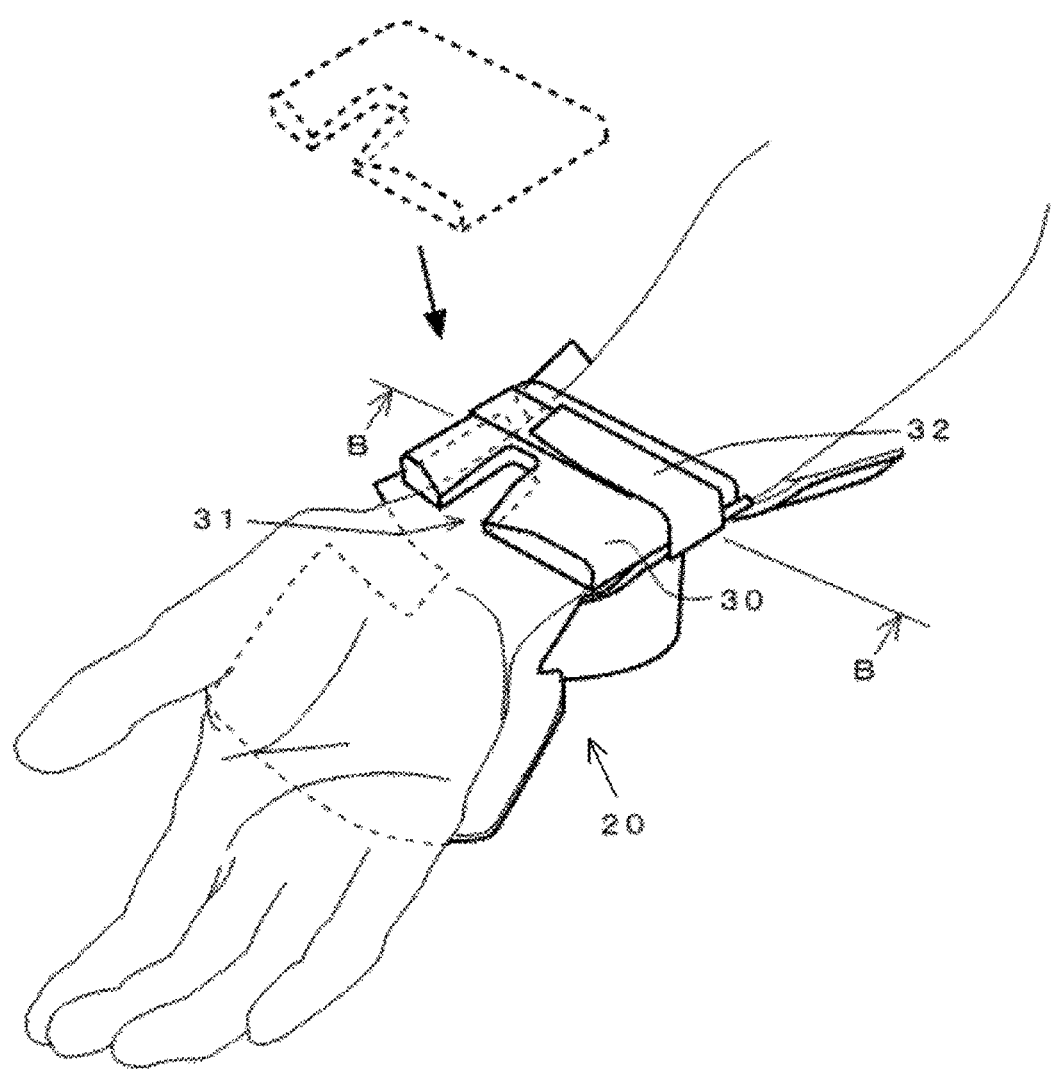
FIG. 6A is a perspective view of a state where a compression member is attached to the wrist placed on the wrist plate.
Figure 8:
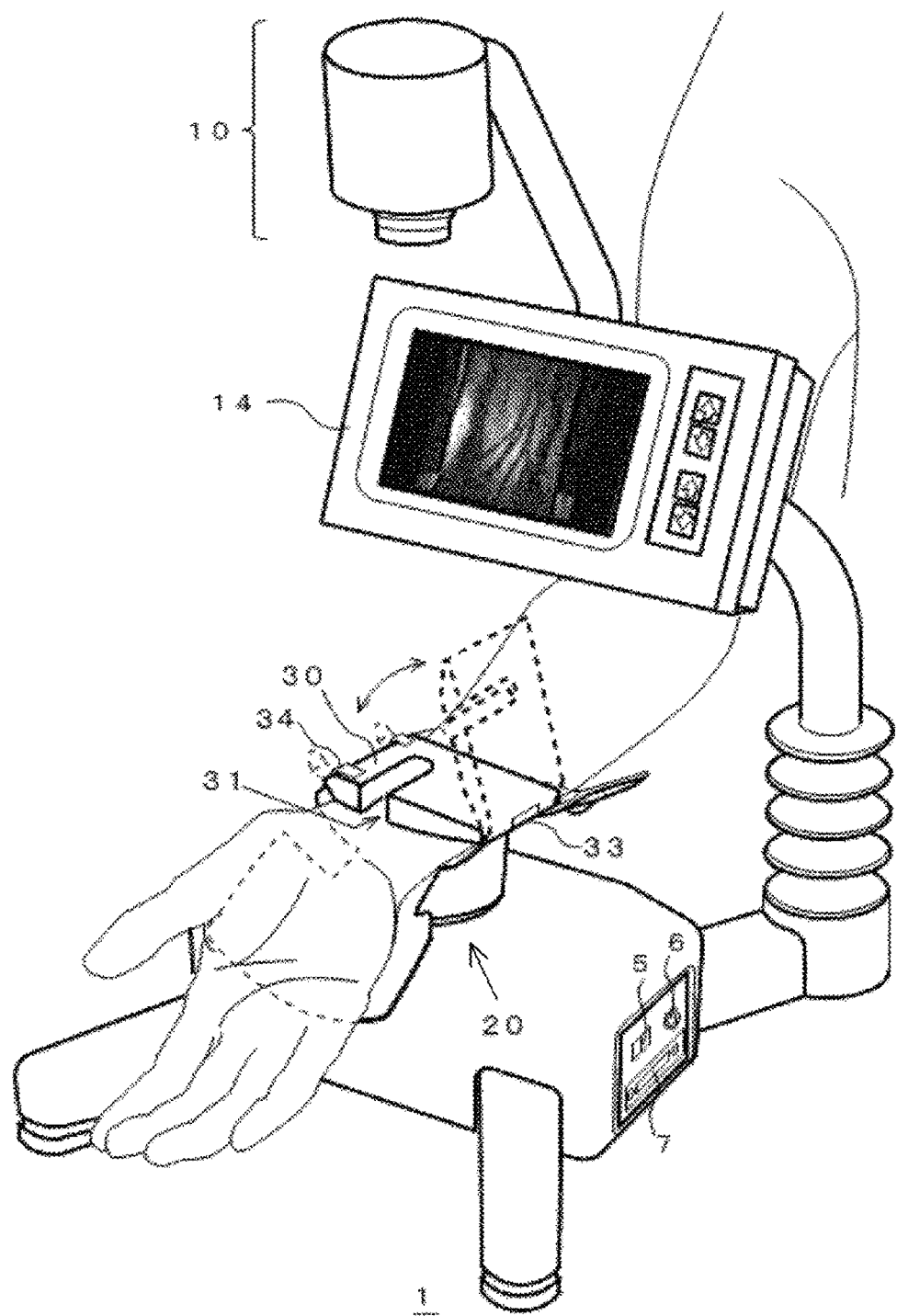
FIG. 8 is an explanatory diagram showing a method for using the artery visualization device according to the embodiment with a compression member.

As shown in FIG. 6A, the artery imaging device may include a compression member 30 which compresses the palm side of the wrist which is placed on the placement table 20 from the back side. This compression member 30 is made of plastic, glass, or the like that transmits near-infrared rays. A notch 31 is preferably formed in the compression member 30 so that a puncture site of the skin can be exposed. The compression member 30 may be configured to be detachably attachable to the placement table 20 so that the compression member 30 can be fixed onto the wrist with a belt 32. As shown in FIG. 8, the compression member 30 and the placement table 20 may be connected by a hinge 33 so that the compressing state of the wrist by the compression member 30 can be fixed with a clasp 34.

Figure 6B:
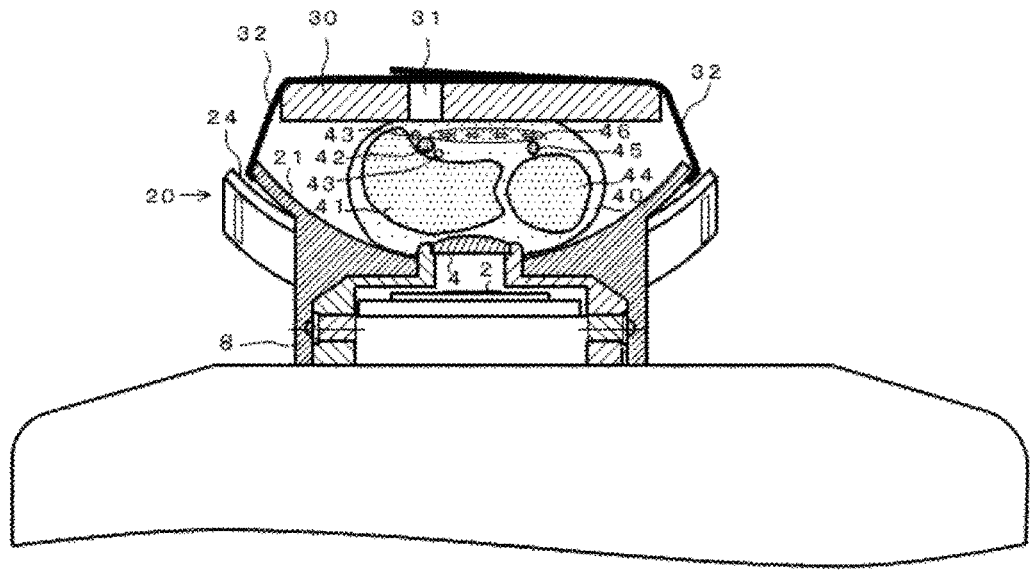
FIG. 6B is a cross-sectional view of the state where the compression member is attached to the wrist placed on the wrist plate.

As shown in FIG. 6B, if the wrist 40 placed on the placement table 20 is also compressed from the palm side by the compression member 30, not only the capillary plexus in the skin between the protrusion 4 and the radius 41 is collapsed but the capillary plexus in the skin between the radius 41 and the compression member 30 is collapsed as well. The artery image can thus be formed more clearly. This facilitates the distinction between the radial artery 42 and the adjoining radial veins 43 in the artery image. In FIG. 6B, the reference numeral 44 represents the ulna, the reference numeral 45 represents the ulnar artery, and the reference numeral 46 represents the tendon and the tendon sheath.

In any of the foregoing modes of the present invention, the artery imaging device and the monitor may be independently formed. The monitor may be connected as an external device to the output terminal of the video signal of the artery imaging device. The near-infrared image of the arteries may be transmitted from the output terminal of the video signal by using communication means.

Figure 7:
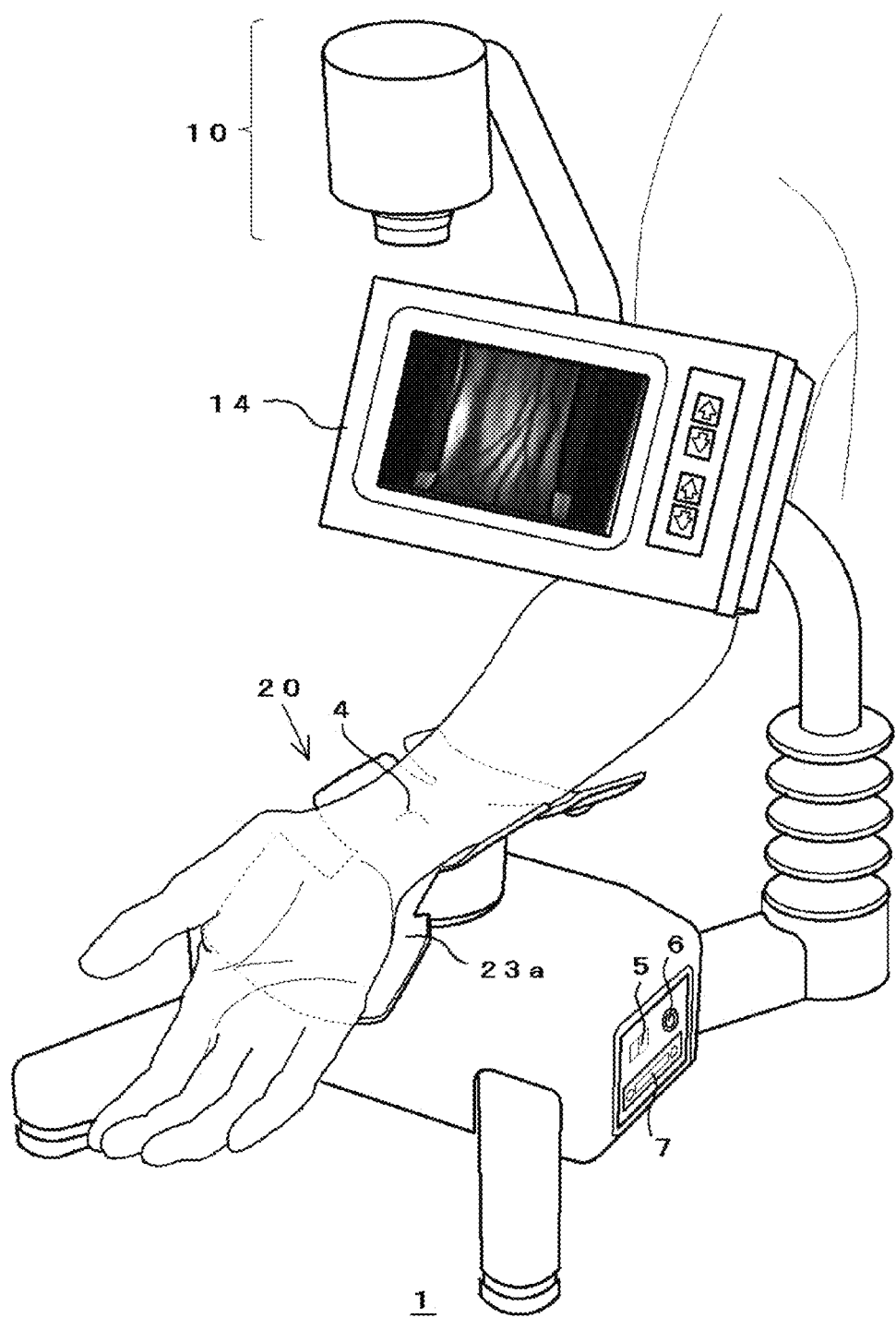
FIG. 7 is an explanatory diagram showing a method for using the artery visualization device according to the embodiment.

In a method for using this artery visualization device 1, as shown in FIG. 7, the subject places the wrist on the placement table 20 and brings the back of the hand into contact with the back of hand contact surface 23a. Alternatively, as shown in FIG. 8, the palm side of the wrist placed on the placement table 20 is further compressed by the compression member 30. Infrared light is made incident on the back side of the wrist from the protrusion 4 of the irradiation unit 3, whereby a near-infrared image of the pulsating arteries is displayed on the monitor 14. The practitioner checks the positions of the arteries from this near-infrared image. By such a simple method, artery puncture can be performed with safety and reliability.

REFERENCE SIGNS LIST 1 artery visualization device
2 light source
3 irradiation unit
4 protrusion
5 power switch
6 DC jack
7 output terminal
8 seat
9 press-fit plunger
10 imaging unit
11 image sensor
12 optical filter
13 lens
14 monitor
15 working space
20 placement table, wrist plate
21 center placement portion
21a wrist placement surface
22 opening
23 back of hand contact portion
23a back of hand contact surface
23p center placement portion-side end of the back of hand contact portion
23q end of the back of hand contact portion
24 forearm placement portion
24a forearm placement surface
24p center placement portion-side end of the forearm placement portion
24q end of the forearm placement portion
25 slit
26 belt
27 seat
28 hole
30 compression member
31 notch
32 belt
33 hinge
34 clasp
40 wrist
41 radius
42 radial artery
43 radial vein
44 ulna
45 ulnar artery
46 tendon, tendon sheath
L1 protruding height of the protrusion
L2 diameter of the protrusion
θ1 angle formed between the back of hand contact surface and the wrist placement surface
θ2 angle formed between the forearm placement surface and the wrist placement surface

The invention claimed is:

1. An artery imaging device comprising:
a placement surface on which a wrist is placed;
an irradiation unit comprising a light source that emits near-infrared light;
an imaging unit comprising an image sensor configured to receive light and form a near-infrared image of the wrist, the light being incident on skin on a back side of the wrist and exiting from skin on a front side; and
an optical filter that is arranged in front of a light receiving surface of the image sensor of the imaging unit, the optical filter being for transmitting near-infrared light, and cutting off visible light, wherein
the placement surface comprises a center placement portion and a back of hand contact portion with which a back of a hand makes contact,
the artery imaging device comprises a protrusion protruding through an opening in the center placement portion, the protrusion compressing the skin on the back side of the wrist placed on the placement surface from the back side of the wrist and irradiating the near-infrared light emitted from the light source to the skin on the back side,
in a vertical cross section passing through the protrusion and longitudinally sectioning the placement surface, a back of hand contact surface of the back of hand contact portion intersects obliquely with a wrist placement surface of the center placement portion, and, with respect to an end of the back of hand contact portion on a side of the center placement portion, an end of the back of hand contact portion on an opposite side lies below the end of the back of hand contact portion on the side of the center placement portion, and
the near-infrared light emitted from the light source passes through the opening in the center placement portion before reaching the skin on the back side.

2. The artery imaging device according to claim 1, comprising a compression member that is made of a material transmitting near-infrared light, the compression member being for compressing a palm side of the wrist placed on the placement surface from the back side of the wrist.

3. The artery imaging device according to claim 1, wherein the wrist placement surface of the center placement portion is curved into a gutter shape having a U-shaped cross section.

4. The artery imaging device according to claim 1, wherein the placement surface includes a forearm placement portion on which a region between the wrist and the elbow is placed, and in the vertical cross section passing through the protrusion and longitudinally sectioning the placement surface, a forearm placement surface of the forearm placement portion intersects obliquely with the wrist placement surface of the center placement portion and, with respect to a center placement portion-side end of the forearm placement portion, an end of the forearm placement portion on the opposite side lies below.

5. The artery imaging device according to claim 1, wherein in the vertical cross section passing through the protrusion and longitudinally sectioning the placement surface, the wrist placement surface of the center placement portion is horizontal.

6. The artery imaging device according to claim 4, wherein the center placement portion, the back of hand contact portion, and the forearm placement portion are formed by an integrally molded wrist plate.

7. The artery imaging device according to claim 6, wherein the wrist plate is detachably attachable.

8. An artery visualization device comprising: the artery imaging device according to claim 1; and a monitor for displaying a near-infrared image of an artery, formed by the artery imaging device.

9. An artery imaging device comprising:
a placement surface on which a wrist is place;
an irradiation unit comprises a light source that emits near-infrared light;
an imaging unit comprising an image sensor configured to receive light and form a near-infrared image of the wrist, the light being incident on skin on a back side of the wrist and exiting from skin on a front side; and
an optical filter that is arranged in front of a light receiving surface of the image sensor of the imaging unit, the optical filter being for transmitting near-infrared light, and cutting off visible light, wherein
the placement surface comprises a center placement portion and a back of hand contact portion with which a back of a hand makes contact,
a wrist placement surface of the center placement portion protrudes to form a protrusion, the protrusion compressing the skin on the back side of the wrist placed on the placement surface from the back side of the wrist, and the near-infrared light emitted from the light source passes through the protrusion to the skin on the back side, and
in a vertical cross section passing through the protrusion and longitudinally sectioning the placement surface, a back of hand contact surface of the back of hand contact portion intersects obliquely with the wrist placement surface of the center placement portion, and, with respect to an end of the back of hand contact portion on a side of the center placement portion, an end of the back of hand contact portion on an opposite side lies below the end of the back of hand contact portion on the side of the center placement portion.

* * * * *